US006296882B1

(12) United States Patent
Viamonte, Jr.

(10) Patent No.: US 6,296,882 B1
(45) Date of Patent: Oct. 2, 2001

(54) NON-TOXIC MUCOSAL DISINFECTANT CONTAINING ISOPROPYL ALCOHOL, SESAME OIL, AND LEMON OIL

(76) Inventor: Manuel Viamonte, Jr., 1643 Brickell Ave., Apart. 2805, Miami, FL (US) 33129

( * ) Notice: Subject to any disclaimer, the term of this patent is extended or adjusted under 35 U.S.C. 154(b) by 0 days.

(21) Appl. No.: 09/591,672

(22) Filed: Jun. 12, 2000

(51) Int. Cl.⁷ .......................... A61K 35/78; A01N 65/00
(52) U.S. Cl. ............................................. 424/736
(58) Field of Search ............................................. 424/736

(56) References Cited

U.S. PATENT DOCUMENTS

| | | |
|---|---|---|
| 3,445,564 | 5/1969 | Kirschner . |
| 4,209,506 | 6/1980 | Bouillon et al. . |
| 4,678,658 | 7/1987 | Casey et al. . |
| 5,145,663 * | 9/1992 | Simmons ................................ 424/47 |
| 5,432,165 * | 7/1995 | Adair et al. ............................ 514/50 |
| 5,441,723 * | 8/1995 | Simmons ................................ 424/47 |

OTHER PUBLICATIONS

John Tummel, M.D., et al., *Ingestion of an Unknown Alcohol*, "Annals of Emergency Medicine", vol. 27:3, pp. 368–374 (Mar., 1996).
L.J. Pereira, et al., *An evaluation of five protocols for surgical handwashing in relation to skin condition and microbial counts*, Journal of Hospital Infection, vol. 36, pp. 49–65 (1997).
Roger J. Price, et al., *Comparison of the toxicity of allyl alcohol, coumarin and menadione in presion–cut rat, guinea–pig, Cynomolgus monkey and human liver slices*, "Arch Toxicol", vol. 71, pp. 107–111 (1996).
Robert W. Kapp, Jr., et al., *Isopropanol: Summary of TSCA Test Rule Studies and Relevance to Hazard Identification*, "Regulatory Toxicology and Pharmacology", vol. 23, pp. 183–192 (1996).
Satomikita, et al., *Antihypertensive Effect of Sesamin. II. Protection against Two–Kidney, One–clip Renal Hypertension and Cardiovascular Hypertrophy*, "Biol. Pharm. Biochem." vol. 8(9), pp. 1283–1285 (1995).
S.R. Chavali, et al., *Decreased Production of Interleukin–1–Beta, Prostaglandin–E, and Thromboxane–$B_2$, and Elevated Levels of Interleukin–6 and 10 are Associated With Increased Survival During Endotoxic Shock in Mice Consuming Diets Enriched with Sesame Oil Supplemented with Quil–A Saponin*, "Int Arch Allerg Immunol", vol. 114, pp. 153–160 (1997).

H. Neering, et al., *Allergens in Sesame Oil Contact Dermatitis*, "Acta Dermatovener (Stockholm)", vol. 55, pp. 31–34 (1975).
T.A. El–Adawy, *Effect of sesame seed proteins supplemental on the nutritional, physical, chemical and sensory properties of wheat flour bread*, "Plant Foods for Human Nutrition", vol. 48, pp. 311–326 (Dec. 1995).
Bernadette Eberlein–König, M.D., et al., *Generalized urticaria caused by seasame seeds with negative prick test results and without demonstrable specific IgE antibodies*, "J Allergy Clin Immunol", vol. 96, No. 4, pp. 560–561 (Oct. 1995).
Afaf Kamal–Eldin, et al., *Sesamin (a compound from sesame oil) Increases Tocopherol Levels in Rats Fed ad libitum*, "Lipids", vol. 30, No. 6, pp. 499–505 (1995).
Subramaniam Satchithanandam, et al., *Effect of Sesame Oil on Serum and Liver Lipids Profiles in the Rat*, "Internat. J. Vit. Nutr. Res", vol. 66, pp. 386–392 (1996).
S. Ten Wolde, F. Engels, et al., *Sesame Oil in Injectable Gold: Two Drugs in One?*. "British Journal of Rheumatology", vol. 36, pp. 1012–1015 (1997).*
G. Kanny, et al., *Sesame seed and sesame seed oil contain masked allergens of growing importance*, "Allergy", vol. 51, pp. 952–957 (1996).*
Michiko Nonaka, et al., *Effects of Dietary Sesaminol and Sesamin on Eicosanoid Production and Immunoglobulin Level in Rats Given Ethanol*, "Biosci. Bicotech Biochem.", vol. 61, No. 5, pp. 836–839 (1997).*
A. Stern, et al., *Evaluation of nasal cytology: a comparison between methods*. "AllergyNet", vol. 53, pp. 325–326 (1998).*
Hirohiko Uaki, et al., *Dose–dependent suppression of toluene metabolism by isopropyl alcohol and methyl ethyl ketone after experimental exposure of rats*, "Toxicology Letters", vol. 81, pp. 229–234, (1995).*
H. Burleigh–Flayer, et al., *Isopropanol Vapor Inhalation Oncogenicity Study in Fischer 344 Rats and CD–1 Mice*, "Fundamental and Applied Toxicology", vol. 36, pp. 95–111 (1997).*

* cited by examiner

Primary Examiner—Herbert J. Lilling
(74) Attorney, Agent, or Firm—Gipple & Hale; John S. Hale

(57) ABSTRACT

A non-toxic mucosal disinfectant for topical application in the nose comprising a composition of 91% isopropyl alcohol of at least 50% by weight; sesame oil not exceeding 49.5% by weight and lemon oil of about 0.5% by weight. All of the components are mixed homogeneously with the sesame oil supplementing and neutralizing the dehydrating effect of the alcohol.

12 Claims, No Drawings

NON-TOXIC MUCOSAL DISINFECTANT CONTAINING ISOPROPYL ALCOHOL, SESAME OIL, AND LEMON OIL

FIELD OF THE INVENTION

The present invention is generally directed toward a topical disinfectant and more specifically is directed toward a non-toxic mucosal disinfectant effective against various pathogenic organisms which cause infectious processes.

DESCRIPTION OF THE PRIOR ART

Infectious diseases remain the leading cause of death and morbidity. Even the domestication of animals has resulted in a number of illnesses (Diphtheria came from the water buffalo; mycobacteria from ungulates; measles from canine distemper, etc.).

The aerosolization of water in western society, ranging from the widespread use of showers instead of baths to the spraying of products in supermarkets, to air conditioning, has probably played a significant role in the emergence of Legionnaire's disease and mycobacterium avium infection in both normal and immunocompromised hosts. Legionella pneumophila, is an infectious agent of predatory protozoans found widely in nature.

Some microorganisms are pathogens (a microorganism capable of causing disease) but most microorganisms that are seen in the human body are innocuous. For example, more than 600 species of bacteria inhabit the large bowel of a human. Not only are the majority of human microorganisms innocuous but they play useful, if unseen roles. These microorganisms provide a necessary part of the development pathways required for the maturation of human intestinal mucosa and our innate local immune system protects us against harmful microorganisms and helps the digestion of food.

Most of human microbes are commensal. Commensal or transient microbes can be an opportunistic pathogen of humans; namely, they can cause disease if one or more defense mechanisms are breached by accident, medical intent, or an underlying metabolic or even infectious disorder.

Human beings are exposed to nosocomial as well as nosohusial infections. Many microorganisms are adapted exclusively to humans and other animals and many pathogenic microorganisms have learned to circumvent, exploit, subvert or avoid our normal cellular mechanisms to multiply at human expense. Some microbes have made the transition from harmless commensal to potentially fatal infectious agents.

Increases in the world population, rapid travel between distant regions, high concentration of individuals in small areas, the wide spread use of air conditioning and heating equipment without air exchange, the large number of people traveling in confined areas (i.e., aircraft, trains, buses, and automobiles), have resulted in the increase in the number of pathogenic organisms and the increase of mutations of organisms. Thus, there is a need for effective protective measures to decrease the number and severity of respiratory infections.

Some societies use face masks as a protection against respiratory infections. However, the use of face masks are an impractical, inefficient and largely ineffective way to prevent dissemination of infection.

There are a number of highly contagious respiratory infections which result in fatal illness, such as African Ebola viruses. Some people have a decreased or defective immunological response to such infections. People who reside in high density cities are at risk for a large variety of respiratory illnesses. Many of the respiratory illnesses do not become confined to the respiratory tract (upper and/or lower) and can disseminate to other organs or become systematic infections.

It is estimated that over 66 million colds occur annually in the United States. An American catches an average of two to four colds a year. As few as ten cold viruses may be enough to cause infection. When symptoms first become noticeable there are thousands of viruses in the lung. The droplets of a sneeze travel as fast as 150 feet a second and as far as 12 feet.

It is highly desirable to protect the nasal mucosa from pathogenic organisms. In those individuals with active respiratory infection, it is also desirable to decrease the likelihood of dissemination of infection by decreasing the number and/or virulence of the pathogenic organisms expelled during exhaling, sneezing, and/or coughing through the use of a topically applied nasal disinfectant and to also reduce or eliminate disease transmissions through the fingers and hand of an infected person.

BACKGROUND OF THE INVENTION

Respiratory infections are the result of the exposure to pathogenic bacteria, viruses, and fungi. The immunological response to infections consists of the neutralization and destruction of the invader by immunoglobulins circulating in the liquid part of the blood (plasma) and phagocytosis from neutrophils, monocytes, and tissue macrophages. When the infection exceeds the effectiveness of the defense mechanism, illness will result.

Good health, and particularly a strong immunological system, is protective against infections. However, at this time, we cannot avoid the effects of the inhalation of pathogens, particularly when subjects are in a closed environment (buildings, airplanes, buses, trains, etc.) or are in physical proximity to individuals who have active respiratory infections and are sneezing, coughing, and expelling microdroplets with a high concentration of pathogens.

Prophylaxi is better than treatment and it appears to be quite limited for the prevention of upper and lower respiratory tract infections. Avoidance of environments with a high concentration of airborne pathogenic material is not always possible. However, the application of a topical antiseptic solution to the nose and avoidance of introducing pathogenic material into the nose by fingers that may be contaminated, appear to be a valid, simple, inexpensive practical method of helping human beings to prevent upper respiratory infection.

When considering the application of a disinfectant to a human subject, it must be recognized that the human capacity for smell is highly developed and easily desensitized which limits the use of a number of disinfectants. Humans have roughly 1000 receptors capable of recognizing some 10,000 distinct odors and over five million smell-sensing cells having neurons with eight or more stringy cilia. Olfactory neurons undergo constant renewals with an average replacement every one to two months. Olfactor receptor cells have bipolar neurons that are located in the olfactory epithelium under the dorsal aspect of the nasal cavity, the septum and part of the superior turbinates in the nose. Turbinates in the nose create airflow patterns that allow volatile compounds to reach the olfactory cells. Olfactory receptors bind odorants and belong to the 2-G-protein-coupled receptor superfamily associated with the adenyl cyclase and phosophoisoniositol signaling. Coding for odor quality and identification may involve the specific temporal sequences of firing that is compound specific. Axons of olfactory bipolar cells traverse through the small holes in the cribiform plate of the ethmoidal bone to the olfactory bulb where they form synapses in intricate masses called glomeruli. There is, thus, a neuroanatomical overlap which provides an anatomical basis for the capacity of odor to produce hedonic responses. Olfactory information is ultimately transmitted to the hypothalamus and this anatomical structure emphasizes the importance of olfaction in eating and nutrition. Thus, it is extremely important when treating disease that these sensor functions are not desensitized or overpowered by the chemical compound being used to treat the infection.

Rubbing alcohol (isopropyl alcohol, isopropanol) is used as a 70% mixture with water for rubdowns because it cools the skin by evaporation and causes pores to close. Isopropyl alcohol has been used for preparing needles and syringes for hypodermic injection. Isopropyl alcohol does not contain ethyl or grain alcohol. It is also used as a solvent for medicine, as a sterilant for instruments and as a skin cleanser before drawing blood or giving injections. Isopropyl alcohol has been shown to be an excellent antiseptic product. It appears to be lethal to bacterial, fungi and viruses, including the AIDS virus. It has also been effectively used as a solution and as a spray for its antiseptic properties as is shown in U.S. Pat. Nos. 5,441,723 and 5,145,663. It is a disinfectant which is nontoxic, biodegradable, material compatible and highly effective.

The use of topical disinfectants for application to body surfaces is noted in:

U.S. Pat. No. 3,445,564 shows various spray germicides used for sanitizing surfaces.

U.S. Pat. No. 4,209,509 describes Aerosol sprays including an anhydrous alcohol used with a fragrance or perfume.

U.S. Pat. No. 4,678,658 shows numerous disinfecting compounds which are effective as germicides for disinfecting surfaces.

U.S. Pat. No. 5,145,663 describes biodegradable disinfectant containing anhydrous alcohol and propylene glycol for use on skin and hard surfaces.

U.S. Pat. No. 5,441,723 shows a composition of various alcohol, propylene glycol; 1,3 Propanediol; 1,2 butanediol PEG 400; glycerol 1,4 butanediol or mixtures all of which reduce the surface glaze formed by alcohol as well as surface tension to be used on body surfaces and hard surfaces.

An examination of the prior art fails to present an effective, non-toxic, disinfectant topically applied through a spray or contact application.

The present invention is based on the discovery that animals and humans have a limited ability to neutralize high concentrations of airborne pathogens and that the present invention can effectively destroy airborne pathogenic material.

SUMMARY OF THE INVENTION

The present invention relates to a non-toxic mucosal disinfectant topically applied which effectively destroys various pathogenic organisms and which does not quickly evaporate and does not interfere with sensory identification of odors.

The non-toxic topical disinfectant comprises a novel composition of isopropyl alcohol, sesame oil and lemon oil, in specific relative proportions by weight. The non-toxic topical solution may be used safely to disinfect the nasal mucosa through application of spray or droplets. The interactive composition comprises of 50% isopropyl alcohol, 49.5% sesame oil, and 0.5% of lemon oil by weight.

It is an object of this invention is to prophylactically apply a solution of the composition comprising isopropyl alcohol, sesame oil, and lemon oil to the distal nasal mucosa (close to the nares) to destroy pathogenic bacteria viruses and fungi which are present therein and which are inhaled. Normally, present flora is destroyed as well, but repopulates the nose, generally 6 hours after the use of the topical disinfectant.

The present invention provides a method of utilizing a disinfectant for the prevention of upper respiratory tract infection.

It is another object of the present invention to treat skin infections with the present inventive composition.

It is also an object of the invention to treat paronychia infection around the fingers or toenails with the inventive composition.

It is yet another object of the invention to provide for the relief of pain and for the treatment of infections in the external auditory canal.

These and other objects, advantages, and novel features of the present invention will become apparent when considered with the teachings contained in the detailed disclosure.

DETAILED DESCRIPTION OF THE PREFERRED EMBODIMENT

Numerous disinfectants and delivery systems have been developed aimed at destroying various pathogenic organisms. The chemical and biological effectiveness of such disinfectants are limited by their chemical and biological effects.

The invention of this non-toxic disinfectant composition, by virtue of its most active ingredient (isopropyl alcohol) is effective against various pathogenic organisms which include bacteria (salmonella, staph, pseudomonas, etc.) viruses, (including herpes, and HIV), and fungi, by topical application of this product in the nasal mucosa. The preferred embodiment of the composition comprises 91% isopropyl alcohol 50% by weight, sesame oil 49.5% by weight and lemon oil 0.5% by weight. Other testing has shown effective treatment with isopropyl alcohol being used in a range of about 50 to 75% weight; sesame oil in the range of about 49.5%+ to 24.5%+ and lemon oil in a range of about 0.1 to 0.5%.

The isopropyl alcohol provides the primary bactericidal and virucidal effect (the killing effect of pathogenic organisms) while sesame oil provides lubrication of the nasal mucos or infection area while also acting as a disinfectant. The dehydrating effect of isopropyl alcohol is also neutralized by its dilution with the sesame oil. The lemon oil which is added to the composition provides lubrication, fragrance and vitamin C to the nasal mucosa. Both the sesame oil and lemon oil provide prolonged contact time of the alcohol to the nasal mucosa or infection area (in excess of four hours up to six hours).

It can, thus be seen that non-toxic mucosal disinfectant of the subject inventive composition includes three distinct products which actively complement each other. One is the primarily active disinfectant, isopropyl alcohol. The others, an additional disinfectant, sesame oil, mixed together with lemon oil, provide mucosal protection which delay the evaporation of the alcohol. The lemon oil adds Vitamin C to the infection site which is effective against infections.

Sesame Oil, Ben (n) e, Gingelly, Simsin, til or ufuta Oil is the oil extracted from the seeds of Sesamum indicum (Pedalialceae). Sesame Oil is an oily product which has 22% total fat, 10% of saturated fat, and polyunsaturated and monounsaturated fat. It has no sodium and no carbohydrate as well as no protein and is not a significant source of cholesterol, dietary fiber, vitamin A and C, calcium and iron. The best sesame oil is the 100% pure expeller pressed.

Lemon Oil is an essential oil meaning containing the essence of lemons. It takes 1000 pounds of fresh lemons to make 10 pounds of pure lemon oil. This oil is derived primarily from lemon peels and contains no scents or preservatives. The lemon oil used in the present composition should be 100% pure USP Grade.

The disinfectant isopropyl alcohol, when used by itself in a 91% solution, is an irritant to the nasal mucosa and its strong scent generally would make it unacceptable. Also, individuals should not be subjected to prolonged inhalation of vapors of any type of alcohol.

Alcohol and oil do not interact chemically and the composition must be thoroughly mixed. A mixture of sesame oil and isopropyl alcohol not only dilutes the alcohol but provides a lubricating surface to the mucosa of the distal part of the nose. When lemon oil is added to these other two ingredients, it contributes to the lubrication of the surface and introduces a scent which makes the combination of substances more agreeable, without harming the sensory receptors. Furthermore, lemon oil has Vitamin C which has well-known beneficial properties, including protection against infections. Preparation of the composition is shown in the following illustrative examples.

EXAMPLE I

The disinfectant properties of the present composition in the dosage recommended (one to three drops in each nasal cavity), occur without toxic effects or damage to the mucosal surface of the nose. The optimum proportional relationships of the ingredients by weight is isopropyl alcohol, 50%; sesame oil, 49.5% and lemon oil, 0.5%. The components are mixed at an ambient temperature with a standard mixing apparatus and topically applied as follows:

The composition of Example I was topically applied by an eye dropper to the external nasal mucosa of a human subject. The nose was then squeezed using sterile gloves to provide a uniform distribution of the solution in the nose.

Subject A, a human male, had a baseline sampling of his right nostril taken at 8:00 a.m. Five minutes after the instillation of inventive solution into his right nostril (Sample 1), another sample was obtained (Sample 2). One hour later, Sample 3 was obtained from the right nostril and at two hours (Sample 4), three hours (Sample 9), four hours (Sample 10), five hours (Sample 11), and at six hours (Sample 12).

The left nostril of Subject A was used as a control. A baseline sample was obtained from the left nostril (Sample 5). Five minutes after using distilled water in the left nostril another sample was obtained (Sample 6). One hour later another sample was obtained from the left nostril (Sample 7). Finally, at two hours, another sample was obtained from the left nostril (Sample 8).

Subject B was a human woman with acute, severe, upper respiratory infection. Topical application of the inventive solution was undertaken in the same manner of application to Subject A. Sample 13 was obtained from the right nostril as a baseline. Ten minutes after application of the inventive solution in the right nostril another sample was obtained (Sample 14). One hour later another sample was obtained from the right nostril (Sample 15). Finally, a two hour sample was obtained from the right nostril (Sample 16). The 28 and 48 hour result showed growth of bacteria. The culture was an Agar blood medium (red background). Colonies of bacteria were visually obvious in the four Agar plates. Each plate was divided into four quadrants:

Plate 1: Samples 1 through 4
Plate 2: Samples 5 through 8
Plate 3: Samples 9 through 12
Plate 4: Samples 13 through 16

The growth of bacteria was classified as few, moderate, or heavy.

RESULTS

Sample 1: Heavy growth (baseline)
Sample 2: Moderate growth (five minutes after instilling the inventive solution)
Sample 3: One hour later and showed moderate growth
Sample 4: Two hours later and showed minimal growth

CONTROL STUDY (After using Water)

Sample 5: Heavy growth
Sample 6: Heavy growth
Sample 7: Moderate growth (one hour after water)
Sample 8: Moderate growth (one hour after water)
Samples 9, 10, 11 and 12 from right nostril.
Sample 9: Minimal growth (three hours)
Sample 10: Moderate growth (four hours)
Sample 11: Moderate growth (five hours)
Sample 12: Minimal growth (six hours)

The Subject B with upper respiratory infection showed heavy growth in Sample 13 (baseline); heavy growth on Sample 14 (10 minutes after instilling the inventive solution. Very minimal growth was present one hour after instilling solution, rare growth (two hours after the inventive solution)- Sample 16.

CONCLUSIONS

1. The present inventive solution is effective in decreasing bacterial growth when compared to normal bacterial growth occurring in the instillation of distilled water.

2. The present inventive solution showed dramatic control on the bacterial growth on the Subject B with acute respiratory infection.

3. The duration of the effects of the inventive solution is as follows:
   a. In the normal subject, four hours after instilling the inventive solution only moderate bacterial growth was observed.
   b. In the Subject B with acute respiratory infection up to two hours, there was insignificant growth of bacteria. The subject with respiratory infection was studied only during the first two hours after instilling the inventive solution.

Photographs were obtained of the four plates and of the individual plates showing the growth of bacteria. There were no studies performed on fungi or viruses.

IN SITU APPLICATION OF INVENTIVE SOLUTION

In the Agar/Blood plates with Samples 13 and 14, drops of the inventive solution were applied to Sample 13 and drops of Virahol®, a commonly used disinfectant, were applied to Sample 14. Both samples showed complete destruction of bacteria within one hour.

The effectiveness of isopropyl alcohol on destroying bacteria, fungi, and viruses, make it an ideal substance to be applied in a topical form to the distal part of the nose. The oily components of this solution (sesame and lemon) produce a type of lubrication which lasts several hours (in general, more than four).

EXAMPLE II

The solution was prepared with a range of isopropyl alcohol of 50 to 75% by weight; sesame oil in a 25 to 49.5% range and lemon oil in a range of 0.1 to 0.5% by weight. A comparative 40% alcohol solution was effective up to two hours. A 30% alcohol solution was effective only for one hour. Two other concentrations, a 20% and a 10% alcohol solutions were not effective at all.

EXAMPLE III

The base solution (50% alcohol) of Example II and higher concentrations of the isopropyl alcohol (65–75%) sesame oil 24.5 to 34.5%, lemon oil about 0.5% appear to be effective against numerous pathogenic organisms when applied to the skin or hard surfaces.

EXAMPLE IV

The solution of Example I was topically applied with an applicator to a skin infection of several human subjects. The infections were cured by the inventive solution.

EXAMPLE V

The solution of Example I was topically applied with an applicator to a fingernail infection of several human subjects. The paronychia was quickly cured.

EXAMPLE VI

The solution of Example I was instilled into the external auditory canal of three subjects with ear pain secondary to infections of the external auditory canal. Within minutes the pain disappeared in all the three patients and the infection was used within the first day.

EXAMPLE VII

The solution of Example I was topically applied with an applicator to aphthous ulcers of the buccal mucosal and the infection was cured.

Several spouses who slept next to a spouse with an upper respiratory infection had the inventive solution applied to both. The unaffected spouse did not develop symptoms of a cold up to two weeks of observation.

In the foregoing description, the invention has been described with reference to a particular preferred embodiment, although it is to be understood that specific details as shown are merely illustrative, and the invention may be carried out in other ways without departing from the true spirit and scope of the following claims.

What I claim is:

1. A non-toxic mucosal disinfectant for topical application in the nose comprising a composition of isopropyl alcohol of at least 50% by weight; sesame oil not exceeding 49.5% by weight and lemon oil not exceeding 0.5% by weight, mixed homogeneously, said sesame oil supplementing and neutralizing the dehydrating effect of the alcohol.

2. A non-toxic topical mucosal disinfectant according to claim 1, wherein said isopropyl alcohol ranges from about 50 to 75% by weight, said sesame oil ranges from about 24.9% to 49.9% by weight.

3. A non-toxic topical mucosal disinfectant according to claim 1, wherein at least 50% by weight of said disinfectant is a 91% isopropyl alcohol and not more than 50% by weight consists of sesame oil and lemon oil.

4. A non-toxic topical mucosal disinfectant according to claim 1, wherein said composition has an effective treatment life of at least four hours and a shelf life of at least two years.

5. A disinfectant composition for treatment of an infection for topical application in the human nose comprising a composition of a solution of isopropyl alcohol of about 50% by weight; sesame oil of about 49.5% by weight and lemon oil of about 0.5% by weight, mixed homogeneously, said sesame oil supplementing and neutralizing the dehydrating effect of the isopropyl alcohol.

6. A non-toxic topical mucosal disinfectant according to claim 5, wherein said composition has an effective treatment life of at least four hours.

7. A non-toxic topical mucosal disinfectant according to claim 5, wherein said isopropyl alcohol is at least 91% pure isopropyl alcohol.

8. A non-toxic topical disinfectant comprising a non-toxic topical disinfectant comprising a composition of a solution of isopropyl alcohol ranging from 50 to 75% by weight, sesame oil ranges from about 24.9% to 49.9% by weight and lemon oil ranging from about 0.1% to 0.5% by weight, said sesame oil supplementing and neutralizing the dehydrating effect of the isopropyl alcohol.

9. A non-toxic topical disinfectant composition for treatment of an infection comprising a non-toxic topical disinfectant according to claim 8, with about 50% by weight of said disinfectant being 91% isopropyl alcohol and about 50% by weight of said disinfectant consisting of sesame oil and lemon oil.

10. A non-toxic topical disinfectant according to claim 8, wherein said isopropyl alcohol is present in a range of about 65 to 75%.

11. A non-toxic topical disinfectant according to claim 8, wherein said lemon oil is present in said composition at about 0.5%.

12. A non-toxic topical disinfectant according to claim 8, wherein said isopropyl alcohol is at least 91% pure isopropyl alcohol.

* * * * *